US012396675B2

(12) United States Patent
Bukofzer et al.

(10) Patent No.: US 12,396,675 B2
(45) Date of Patent: Aug. 26, 2025

(54) METHODS OF ASSESSING HEPATIC ENCEPHALOPATHY

(71) Applicant: AMALIVE LIMITED, Aldridge (GB)

(72) Inventors: Stanley Bukofzer, Hazelwood, MO (US); Regis Vilchez, Hazelwood, MO (US)

(73) Assignee: AMALIVE LIMITED, Aldridge (GB)

( * ) Notice: Subject to any disclaimer, the term of this patent is extended or adjusted under 35 U.S.C. 154(b) by 697 days.

(21) Appl. No.: 17/605,699

(22) PCT Filed: May 7, 2020

(86) PCT No.: PCT/US2020/031854
§ 371 (c)(1),
(2) Date: Oct. 22, 2021

(87) PCT Pub. No.: WO2020/227516
PCT Pub. Date: Nov. 12, 2020

(65) Prior Publication Data
US 2022/0249010 A1    Aug. 11, 2022

Related U.S. Application Data

(60) Provisional application No. 62/845,569, filed on May 9, 2019.

(51) Int. Cl.
| | |
|---|---|
| *A61P 1/16* | (2006.01) |
| *A61B 5/00* | (2006.01) |
| *A61K 31/192* | (2006.01) |
| *A61K 31/198* | (2006.01) |
| *A61K 31/235* | (2006.01) |
| *A61P 25/28* | (2006.01) |

(52) U.S. Cl.
CPC .......... *A61B 5/4076* (2013.01); *A61B 5/4244* (2013.01); *A61B 5/4839* (2013.01); *A61B 5/4842* (2013.01); *A61K 31/192* (2013.01); *A61K 31/198* (2013.01); *A61K 31/235* (2013.01); *A61P 1/16* (2018.01); *A61P 25/28* (2018.01)

(58) Field of Classification Search
CPC .. A61K 31/198; A61K 31/192; A61K 31/235; A61B 5/4076; A61B 5/4244; A61B 5/4839; A61P 1/16
USPC .......................................................... 705/2
See application file for complete search history.

(56) References Cited

U.S. PATENT DOCUMENTS

| | | | |
|---|---|---|---|
| 8,173,706 B2 | 5/2012 | Anderson et al. | |
| 8,389,576 B2 | 3/2013 | Jalan et al. | |
| 8,492,439 B2 | 7/2013 | Anderson et al. | |
| 8,785,498 B2 | 7/2014 | Anderson et al. | |
| 8,946,473 B2 | 2/2015 | Anderson et al. | |
| 9,034,925 B2 | 5/2015 | Anderson et al. | |
| 9,260,379 B2 | 2/2016 | Anderson et al. | |
| 9,566,257 B2 | 2/2017 | Jalan et al. | |
| 9,604,909 B2 | 3/2017 | Anderson et al. | |
| 10,039,735 B2 | 8/2018 | Jalan et al. | |
| 10,173,964 B2 | 1/2019 | Anderson et al. | |
| 10,314,828 B2* | 6/2019 | Forbes | G16H 20/10 |
| 10,525,029 B2 | 1/2020 | Jalan et al. | |
| 10,550,069 B2 | 2/2020 | Anderson | |
| 10,610,506 B2 | 4/2020 | Jalan et al. | |
| 10,835,506 B2 | 11/2020 | Rose et al. | |
| 11,040,021 B2 | 6/2021 | Jalan et al. | |
| 11,066,352 B2 | 7/2021 | Pilsl et al. | |
| 11,161,802 B2 | 11/2021 | Anderson et al. | |
| 11,219,611 B2 | 1/2022 | Wang et al. | |
| 11,266,620 B2 | 3/2022 | Jalan et al. | |
| 2008/0119554 A1 | 5/2008 | Jalan et al. | |
| 2010/0280119 A1 | 11/2010 | Anderson et al. | |
| 2011/0035232 A1 | 2/2011 | Forbes et al. | |
| 2013/0211135 A1 | 8/2013 | Anderson et al. | |
| 2015/0094278 A1 | 4/2015 | Scharschmidt et al. | |
| 2015/0141450 A1 | 5/2015 | Forbes et al. | |
| 2016/0338982 A1 | 11/2016 | Ruettimann et al. | |
| 2016/0354025 A1* | 12/2016 | Scharschmidt | A61P 25/28 |
| 2017/0135973 A1 | 5/2017 | Wang et al. | |

FOREIGN PATENT DOCUMENTS

| | | | |
|---|---|---|---|
| WO | WO 2006/056794 A1 | 6/2006 | |
| WO | WO 2010/115055 A1 | 10/2010 | |

(Continued)

OTHER PUBLICATIONS

Kim C.W., "Hepatic Encephalopathy", The Korean J Med. Jul. 1, 2008;75(1): 27-36.
Rahimi et al., "STOP-HE: A randomized, double-blind, placebo-controlled study of OCR-002 in patients with hepatic encephalopathy." AASLD Abstracts 502, Hepatology Oct. 2017; p. 276A.
Salam et al., "Modified-orientation log to assess hepatic encephalopathy," Alimentary Pharma Thera. Apr. 2012;35(8): 913-920.
Bajaj et al., "Review article: the design of clinical trials in hepatic encephalopathy—an International Society for Hepatic Encephalopathy and Nitrogen Metabolism (ISHEN) consensus statement", Aliment Pharmacol Ther. 2011; 33(7):739-747.

(Continued)

*Primary Examiner* — Mamon Obeid
*Assistant Examiner* — Teresa S Williams
(74) *Attorney, Agent, or Firm* — Knobbe, Martens, Olson & Bear, LLP

(57) ABSTRACT

The present disclosure relates to methods of treating or ameliorating hepatic encephalopathy (HE), including assessing the severity of HE in a patient suffering from HE, or the determining the presence or occurrence of an overt hepatic encephalopathy event. In particular, some aspects of the methods use a novel Hepatic Encephalopathy Staging Tool (HEST), which includes a set of criteria to categorize the HE into different stages and provide guidance on effective treatments based on the severity of the HE. Other aspects of the methods use an Overt Hepatic Encephalopathy Screening Tool (O-HEST) to determine whether an OHE event is occurring or has occurred and provide guidance on proper medical attention and change in treatment.

15 Claims, No Drawings

(56) References Cited

FOREIGN PATENT DOCUMENTS

| WO | WO 2010/144498 A1 | 12/2010 | | |
|---|---|---|---|---|
| WO | WO 2012/048043 A1 | 4/2012 | | |
| WO | WO 2016/085887 A1 | 6/2016 | | |
| WO | WO 2017/031131 A1 | 2/2017 | | |
| WO | WO-2017053613 A1 | * | 3/2017 | ........... A61K 31/192 |
| WO | WO-2018208677 A1 | * | 11/2018 | ........... C07C 227/16 |
| WO | WO 2020/227516 A1 | 11/2020 | | |
| WO | WO 2021/076709 A1 | 4/2021 | | |
| WO | WO 2021/236522 A1 | 11/2021 | | |

OTHER PUBLICATIONS

Bajaj et al., "Overt hepatic encephalopathy: Development of a novel clinician report outcome tool and electronic caregiver diary", Metab Brain Dis. Jun. 2016; 31:1081-1093.

Hassanein et al., "Performance of the hepatic encephalopathy scoring algorithm in a clinical trial of patients with cirrhosis and severe hepatic encephalopathy", Am J Gastroenterol. 2009; 104(6):1392-1400.

Jalan et al., "L-Ornithine phenylacetate (OP): a novel treatment for hyperammonemia and hepatic encephalopathy," Med Hypoth. 2007; 69(5):1064-1069.

Rockey et al., "Randomized, Double-Blind, Controlled Study of Glycerol Phenylbutyrate in Hepatic Encephalopathy," Hepatol. 2014, 59(3):1073-1083.

International Search Report and Written Opinion dated Jul. 31, 2020 in Application No. PCT/US2020/031854, filed May 7, 2020.

Flamm, S.L. "Rifaximin treatment for reduction of risk of overt hepatic encephalopathy recurrence," Therapeutic Advances in Gastroenterology, 2011, vol. 4(3), pp. 199-206.

Rose, C. "Ammonia-Lowering Strategies for the Treatment of Hepatic Encephalopathy," Clinical Pharmacology & Therapeutics, 2012, vol. 92(3), pp. 321-331.

Wijdicks, E.F. "Hepatic encephalopathy," The New England Journal of Medicine, 2016, vol. 375(17), pp. 1660-1670.

* cited by examiner

METHODS OF ASSESSING HEPATIC ENCEPHALOPATHY

BACKGROUND

Field

The present disclosure relates to the fields of pharmaceutical chemistry, biochemistry, and medicine. In particular, it relates to methods of assessing and treating various stage of hepatic encephalopathy in a patient.

Description

Hyperammonemia is a hallmark of liver disease and is characterized by an excess of ammonia in the bloodstream. Hepatic encephalopathy (HE) is a complex neuropsychiatric disorder that occurs in diverse clinical situations such as acute or chronic liver disease and spontaneous portosystemic venous shunting.

Hepatic encephalopathy (HE), the most common complication of cirrhosis, sometimes is viewed as a primary clinical consequence of progressive hyperammonemia, which may complicate acute or chronic hepatic failure. It is characterized by changes in mental state including a wide range of neuropsychiatric symptoms ranging from minor signs of altered brain function to overt psychiatric and/or neurological symptoms. HE may cause sleep-wake abnormalities, cognitive changes, impair motor function, and can lead to coma.

Hepatic encephalopathy, which is further divided into overt and covert hepatic encephalopathy, has been the subject of considerable debate with respect to terminology, diagnosis criteria, and severity classification (Bajaj et al., Aliment Pharmacol Ther. 2011; 33(7):739-747; Hassanein et al., Am J Gastroenterol. 2009; 104(6):1392-1400). Covert hepatic encephalopathy (CHE) is considered as the preclinical stages of hepatic encephalopathy, while overt hepatic encephalopathy (OHE) is a serious event requiring medical attention and possibly change in treatment. Consensus has been reached regarding some aspects of HE assessment and how treatment effects should be measured in clinical trials.

The West Haven Criteria has been a standard scale used to diagnose and grade HE based on impairment of consciousness, intellectual function, and behavior. The primary criticism is that there is considerable difficulty in the distinction between grades 1 and 2 because the neurological symptoms may be less precise and therefore subject to observer interpretation, and nonspecific signs and symptoms are often used in differentiating between stages leading potentially to a lack of reproducibility and inconsistency. None of the tools currently available to physicians for evaluating severity of HE, including the West Haven (WH) grading system, achieve the necessary level of precision for regulatory approval. Therefore, there remains a need to develop an effective HE grading measurement tool for use in a clinical setting.

SUMMARY

The present disclosure relates to method of treating or ameliorating hepatic encephalopathy (HE) using one or more novel hepatic encephalopathy staging tools (HEST).

Some embodiments of the disclosure relate to methods of treating or ameliorating hepatic encephalopathy in a patient, comprising: assessing the severity of hepatic encephalopathy by using a hepatic encephalopathy staging tool, said staging tool comprising a first criterion, a second criterion, a third criterion and a fourth criterion; and administering to said patient an effective amount of a medicament to treat or ameliorate hepatic encephalopathy; wherein the first criterion comprises a first set of factual questions and the first criterion is met when the patient verbally answers all the first set of factual questions correctly and the patient does not have asterixis; wherein the second criterion comprises a second set of factual questions and the second criterion is met when the patient fails to verbally answer all the second set of factual questions correctly and the patient has asterixis; wherein the third criterion is met when at least one symptom is observed or has been observed in the patient, the symptom is selected from the group consisting of stupor, severe drowsiness, obvious confusion, and gross disorientation; and wherein the fourth criterion is met when the patient is in a coma. In some embodiments, the administration of an effective amount of a medicament for treating or ameliorating hepatic encephalopathy is determined by the assessed severity of hepatic encephalopathy.

Some other embodiments of the disclosure relate to methods of treating or ameliorating hepatic encephalopathy in a patient, comprising: receiving information regarding the severity of hepatic encephalopathy in the patient, wherein the severity of hepatic encephalopathy is assessed by a hepatic encephalopathy staging tool, said staging tool comprising a first criterion, a second criterion, a third criterion and a fourth criterion; and administering to said patient an effective amount of a medicament to treat or ameliorate hepatic encephalopathy; wherein the first criterion comprises a first set of factual questions and the first criterion is met when the patient verbally answers all the first set of factual questions correctly and the patient does not have asterixis; wherein the second criterion comprises a second set of factual questions and the second criterion is met when the patient fails to verbally answer all the second set factual questions correctly and the patient has asterixis; wherein the third criterion is met when at least one symptom is observed or has been observed in the patient, the symptom is selected from the group consisting of stupor, severe drowsiness, obvious confusion, and gross disorientation; and wherein the fourth criterion is met when the patient is in a coma. In some embodiments, the administration of an effective amount of a medicament is determined by the assessed severity of hepatic encephalopathy.

Some further embodiments of the disclosure relate to methods of treating hepatic encephalopathy in a patient, comprising: administering to said patient an effective amount of a medicament to treat hepatic encephalopathy; and assessing the severity of hepatic encephalopathy by using a hepatic encephalopathy staging tool, said staging tool comprising a first criterion, a second criterion, a third criterion and a fourth criterion; wherein the first criterion comprises a first set of factual questions and the first criterion is met when the patient verbally answers all the first set of factual questions correctly and the patient does not have asterixis; wherein the second criterion comprises a second set of factual questions and the second criterion is met when the patient fails to verbally answer all the second set of factual questions correctly and the patient has asterixis; wherein the third criterion is met when at least one symptom is observed or has been observed in the patient, the symptom is selected from the group consisting of stupor, severe drowsiness, obvious confusion, and gross disorientation; and wherein the fourth criterion is met when the patient is in a coma. In some embodiments, the assessment of the stage of hepatic encephalopathy after administration of the medicament may evaluate the effectiveness of the hepatic encephalopathy treatment. In some further embodiments, the method further comprises adjusting the amount of the medicament based on the effectiveness of the hepatic encephalopathy treatment.

Some embodiments of the disclosure relate to methods of treating or ameliorating hepatic encephalopathy in a patient, comprising: assessing the severity of hepatic encephalopathy by using a hepatic encephalopathy staging tool, said staging tool comprising a first criterion, a second criterion, a third criterion and a fourth criterion; and administering to said patient an effective amount of a medicament to treat or ameliorate hepatic encephalopathy; wherein the first criterion comprises a first set of factual questions and the first criterion is met when the patient verbally answers all the first set of factual questions correctly, or when the patient verbally answers only one factual questions incorrectly; wherein the second criterion comprises a second set of factual questions and the second criterion is met when the patient answers two or more factual questions incorrectly; wherein the third criterion is met when at least one symptom is observed or has been observed in the patient, the symptom is selected from the group consisting of stupor, severe drowsiness, obvious confusion, and gross disorientation; and wherein the fourth criterion is met when the patient is in a coma. In some embodiments, the administration of an effective amount of a medicament for treating or ameliorating hepatic encephalopathy is determined by the assessed severity of hepatic encephalopathy.

Some other embodiments of the disclosure relate to methods of treating or ameliorating hepatic encephalopathy in a patient, comprising: receiving information regarding the severity of hepatic encephalopathy in the patient, wherein the severity of hepatic encephalopathy is assessed by a hepatic encephalopathy staging tool, said staging tool comprising a first criterion, a second criterion, a third criterion and a fourth criterion; and administering to said patient an effective amount of a medicament to treat or ameliorate hepatic encephalopathy; wherein the first criterion comprises a first set of factual questions and the first criterion is met when the patient verbally answers all the first set of factual questions correctly, or when the patient verbally answers only one factual questions incorrectly; wherein the second criterion comprises a second set of factual questions and the second criterion is met when the patient answers two or more factual questions incorrectly; wherein the third criterion is met when at least one symptom is observed or has been observed in the patient, the symptom is selected from the group consisting of stupor, severe drowsiness, obvious confusion, and gross disorientation; and wherein the fourth criterion is met when the patient is in a coma. In some embodiments, the administration of an effective amount of a medicament is determined by the assessed severity of hepatic encephalopathy.

Some further embodiments of the disclosure relate to methods of treating hepatic encephalopathy in a patient, comprising: administering to said patient an effective amount of a medicament to treat hepatic encephalopathy; and assessing the severity of hepatic encephalopathy by using a hepatic encephalopathy staging tool, said staging tool comprising a first criterion, a second criterion, a third criterion and a fourth criterion; wherein the first criterion comprises a first set of factual questions and the first criterion is met when the patient verbally answers all the first set of factual questions correctly, or when the patient verbally answers only one factual questions incorrectly; wherein the second criterion comprises a second set of factual questions and the second criterion is met when the patient answers two or more factual questions incorrectly; wherein the third criterion is met when at least one symptom is observed in the patient, the symptom is selected from the group consisting of stupor, severe drowsiness, obvious confusion, and gross disorientation; and wherein the fourth criterion is met when the patient is in a coma. In some embodiments, the assessment of the stage of hepatic encephalopathy after administration of the medicament may evaluate the effectiveness of the hepatic encephalopathy treatment. In some further embodiments, the method further comprises adjusting the amount of the medicament based on the effectiveness of the hepatic encephalopathy treatment.

Some additional embodiments of the disclosure relate to methods of treating or ameliorating hepatic encephalopathy in a patient in need thereof, comprising: determining the presence of an overt hepatic encephalopathy event by using a hepatic encephalopathy screening tool comprising a first assessment and a second assessment; and administering to said patient an effective amount of a medicament to treat or ameliorate hepatic encephalopathy when the presence of an overt hepatic encephalopathy event is present or has occurred; wherein the first assessment comprises using a set of factual questions to determine whether the patient is disoriented to time or place, and the second assessment comprises determining the level of consciousness of the patient; and wherein the hepatic encephalopathy screening tool does not require observation or determination of asterixis.

Some further embodiments of the disclosure relate to methods of treating or ameliorating hepatic encephalopathy in a patient in need thereof, comprising: receiving information regarding the presence of an overt hepatic encephalopathy event in the patient, wherein the presence of an overt hepatic encephalopathy event is determined by a hepatic encephalopathy screening tool, said screening tool comprising a first assessment and a second assessment; and administering to said patient an effective amount of a medicament to treat or ameliorate hepatic encephalopathy when the presence of an overt hepatic encephalopathy event is present or has occurred; wherein the first assessment comprises using a set of factual questions to determine whether the patient is disoriented to time or place, and the second assessment comprises determining the level of consciousness of the patient; and wherein the hepatic encephalopathy screening tool does not require observation or determination of asterixis.

In any embodiments of the methods described herein, the medicament for treating or ameliorating hepatic encephalopathy includes an ammonia lowering agent. In some further embodiments, the ammonia lowering agent is L-ornithine phenylacetate.

DETAILED DESCRIPTION

Some aspects of the present disclosure relate to methods of treating or ameliorating hepatic encephalopathy (HE) using one or more novel hepatic encephalopathy staging tools, a clinician-reported outcome measure for assessment of HE stage. The HE staging tools may be used for assessment of overt hepatic encephalopathy sufficient to warrant hospital admission, i.e., hospital grade acute episodes of HE. It uses concrete content based on a distillation of common medical practice in a standardized way, to achieve a simple, readily applicable approach to HE assessment in this setting.

Some other aspects of the present disclosure relate to methods of treating or ameliorating HE using an overt hepatic encephalopathy screening tool (OHEST or O-HEST). The OHEST may be used in clinical trials evaluating prophylactic treatment of HE where it is important to identify when a patient transitions from covert HE (CHE) to overt HE (OHE). Documenting the rate of occurrence or recurrence of OHE is an important step to understanding benefit or effect of prophylactic treatments. The OHEST may be used as a clinician-reported tool to identify the presence or absence of an OHE event.

Definitions

The section headings used herein are for organizational purposes only and are not to be construed as limiting the subject matter described.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, formulation, or device, the term "comprising" means that the compound, composition, formulation, or device includes at least the recited features or components, but may also include additional features or components.

As used herein, common abbreviations are defined as follows:
CT Confidence interval
GCS Glasgow Coma Scale
HE Hepatic encephalopathy
HEST Hepatic encephalopathy staging tool
MO-log Modified orientation log
OTE Overall treatment evaluation "Treat," "treatment," or "treating," as used herein refers to administering a pharmaceutical composition/formulation for prophylactic and/or therapeutic purposes. The term "prophylactic treatment" refers to treating a patient who is not yet suffering from a disease, but who is susceptible to, or otherwise at risk of, a particular disease, whereby the treatment reduces the likelihood that the patient will develop a disease. The term "therapeutic treatment" refers to administering treatment to a patient already suffering from a disease.

The term "asterixis" as used herein, refers to a motor disorder characterized by an inability to maintain a position due to a metabolic encephalopathy. It can be elicited on physical exam by asking patients to hold their arms straight to the front with the hands dorsiflexed as far back as possible. When asterixis is present, there will be arrhythmically occurring "flaps" of the hands downwards, followed after a brief but distinct moment by recovery back to the dorsiflexed position. In some instances, both hands will "flap" down simultaneously. In cases where patients are unable to hold their arms forward, an alternative approach to eliciting asterixis involves having the patient rest the arms prone on the bed and then asking him or her to dorsiflex the hands off the bed, again holding that position for 30 seconds. Myoclonus is distinguished by the fact that it represents not an abrupt loss of tone with a "flap" down, but rather an abrupt gain of tone with a resultant "jerk" up. Tremor is distinguished by the presence of more or less rhythmic oscillatory movement secondary to alternating contraction of agonist and antagonist musculature (Moore D P and Puri B K, Textbook of Clinical Neuropsychiatry and Behavioral Neuroscience, 2012, 3rd edition. London: Taylor & Francis Ltd.). In some embodiments of the hepatic encephalopathy staging tool (HEST) described herein, three or more flaps in thirty seconds is considered positive for asterixis.

The term "stupor" as used herein, refers to the lack of critical mental function and a level of consciousness wherein a sufferer is almost entirely unresponsive and only responds to base stimuli, such as pain. It is characterized by impairments to reactions to external stimuli. In some embodiments of the HEST described herein, a patient is considered to be in a stuporous state if the patient has severe drowsiness (can be aroused by moderate stimuli but then almost immediately drifts back to sleep), or the patient is unresponsive and the patient can be aroused only by vigorous and repeated stimuli, or the patient's speech is incomprehensible.

The term "severe drowsiness" as used herein, refers to a state in which the subject can be aroused by moderate stimuli but then almost immediately drifts back to sleep.

The term "obvious confusion" and "gross disorientation" as used herein, may include behavior such as inappropriate response to questions or commands; bewilderment; inattention to question; or combinations thereof.

As used herein, the term "coma" or "comatose" is defined as a state of unarousable unresponsiveness.

Some embodiments of the disclosure relate to methods of treating or ameliorating hepatic encephalopathy in a patient, including: assessing the severity of hepatic encephalopathy by using a hepatic encephalopathy staging tool described herein; and administering to the patient an effective amount of a medicament (e.g., one or more ammonia lowering agents) to treat or ameliorate hepatic encephalopathy.

Some other embodiments of the disclosure relate to methods of treating or ameliorating hepatic encephalopathy in a patient, including: receiving information regarding the severity of hepatic encephalopathy in the patient, wherein the severity of hepatic encephalopathy is assessed by a hepatic encephalopathy staging tool described herein; and administering to the patient an effective amount of a medicament (e.g., one or more ammonia lowering agents) to treat or ameliorate hepatic encephalopathy.

Some further embodiments of the disclosure relate to methods of treating or ameliorating hepatic encephalopathy in a patient, including: administering to the patient an effective amount of a medicament (e.g., one or more ammonia lowering agents) to treat hepatic encephalopathy; and assessing the severity of hepatic encephalopathy by using a hepatic encephalopathy staging tool described herein.

In some embodiments, the administration of an effective amount of a medicament (e.g., one or more ammonia lowering agents) for treating or ameliorating hepatic encephalopathy is determined by or based on the assessed severity of hepatic encephalopathy.

In some embodiments, the assessment of the stage of hepatic encephalopathy after administration of the medicament may be used to evaluate the effectiveness of the hepatic encephalopathy treatment.

In any embodiments of the methods described herein, the amount of the medicament (e.g., one or more ammonia lowering agents) may be adjusted based on the assessed severity of hepatic encephalopathy or the effective of the treatment.

In any embodiments of the methods described herein, the method may include a step of selecting for treatment a patient suffering form hepatic encephalopathy. In some such embodiments, a hepatic encephalopathy screening tool may be used to determine whether the patient has suffered from or is suffering overt hepatic encephalopathy, such as the overt hepatic encephalopathy screening tool (O-HEST) described herein.

Hepatic Encephalopathy Staging Tools (HEST)

One embodiment of the hepatic encephalopathy staging tool described herein includes four criteria: a first criterion, a second criterion, a third criterion and a fourth criterion. The first criterion comprises a first set of factual questions. The first criterion is met when the patient verbally answers all the first set of factual questions correctly. In some such embodiments, the patient meeting the first criterion also does not have asterixis. The second criterion comprises a second set of factual questions. The second criterion is met when the patient has asterixis and/or fails to verbally answer all the second set of factual questions correctly. The third criterion is met when at least one symptom is observed or has been observed in the patient, including one or more symptoms selected from the group consisting of stupor, severe drowsiness, obvious confusion, and gross disorientation. The fourth criterion is met when the patient is in a coma.

Another embodiment of the hepatic encephalopathy staging tool described herein includes four criteria: a first criterion, a second criterion, a third criterion and a fourth criterion. The first criterion comprises a first set of factual questions. The first criterion is met when the patient verbally answers all the factual questions correctly, or when the patient verbally answers only one factual question incorrectly. The second criterion comprises a second set of factual questions and the second criterion is met when the patient answers two or more questions from the second set of factual questions incorrectly. The third criterion is met when at least one symptom is observed or has been observed in the patient, including one or more symptoms selected from the group consisting of stupor, severe drowsiness, obvious confusion, and gross disorientation. The fourth criterion is met when the patient is in a coma. In this embodiment of the hepatic encephalopathy staging tool, there is no requirement for the observation or determination of whether the patient has asterixis.

In some embodiments of the first criterion described herein, the first set and the second set of factual questions each comprises inquiry to the patient's name, residence, birthday, present location, time, other facts that are commonly and widely known, or combinations thereof. For example, the factual questions may include: "what is your name," "what city are we in," "what type of place is this," "what is the year," "what is the month," "what year were you born," "who is the current president (or country specific leader)" etc. In some such embodiments, the first set and the second set of factual questions may be the same. In some embodiments, the first and the second set of questions may each include 4, 5, 6, 7 or 8 questions. The first criterion is designed to assess whether the patient has any disorientation. When the patient is able to correctly answer all the factual questions or only answer one question incorrectly, the first criterion is met or satisfied. In some embodiments, asterixis is present or diagnosed if three or more involuntary hand flaps are observed in the patient within 30 seconds during assessment.

In some embodiments of the methods described herein, HEST is used to evaluate the severity of hepatic encephalopathy (HE). The severity of hepatic encephalopathy is divided or categorized into a first stage, a second stage, a third stage, and a fourth stage. In some such embodiments, the first stage of hepatic encephalopathy is defined by meeting the first criterion. In some cases, the first stage is further divided into two sub-stages, such as stage 0 and stage 1. A patient categorized as the first stage of HE generally has no disorientation or very minor or mild disorientation. Such patient is generally alert, responsible, and able to engage in conversation with a clinician. In some such embodiments, the second stage of hepatic encephalopathy is defined by meeting the second criterion. A patient categorized as the second stage of HE may be sleepy, but generally is easily arousable. Such patient is able to engage in conversation with a clinician, but may be slower to respond. In some such embodiments, the third stage of hepatic encephalopathy is defined by meeting the third criterion. In some such embodiments, the fourth stage of hepatic encephalopathy is defined by meeting the fourth criterion.

The different criteria described herein are designed to be mutually exclusive, meaning if a patient satisfies one criterion, it is unlikely that he/she will also satisfy the other criteria. For example, a patient is highly unlikely to satisfy both the second criterion and the third criterion because if such patient has any of the symptoms described by the third criterion, it will be unlikely that he/she will be responsive or pay attention to the factual questions.

In one particular example, the HEST described herein comprises the criteria outlined below:

| | |
|---|---|
| Stage 0/1 | No asterixis* and no disorientation based on the following 5 questions (i.e., patient provides correct response to Questions 1, 2, 3, 4, and 5):<br>1. What is your name?<br>2. What city are we in?<br>3. What type of place is this? (correct answer hospital)<br>4. What is the year?<br>5. What is the month? |
| Stage 2 | Asterixis* and disorientation based on the following 5 questions, i.e., any single incorrect response qualifies the patient as Stage 2 for the following questions 1, 2, 3, 4, or 5:<br>1. What is your name?<br>2. What city are we in?<br>3. What type of place is this? (correct answer hospital)<br>4. What is the year?<br>5. What is the month? |
| Stage 3 | Stupor, arousable but falls asleep, responsive to verbal stimuli<br>Obvious confusion<br>Gross disorientation |
| Stage 4 | Coma |

*Observe for 30 seconds; 3 or more flaps in that timeframe considered positive for asterixis.

In another example, the HEST described herein comprises the criteria outlined below. This version of HEST does not rely on the presence or absence of asterixis in the determination of HE severity.

| | |
|---|---|
| Stage 0/1 | Patient to be considered Stage 0/1 if any of the following apply:<br>No Disorientation (i.e., all correct answers for questions 1 through 7)<br>Mild Disorientation (i.e., one incorrect answer for questions 1 through 7)<br>1. What is your name?<br>2. What year were you born?<br>3. What city or town do you live in?<br>4. What type of place is this?<br>5. What is the year?<br>6. Who is the current president (or country-specific leader)?<br>7. What is the month?<br>Note: Patients who are in Stage 0/1 will be alert, responsive, and able to engage in conversation with clinical staff. |
| Stage 2 | Patient to be considered Stage 2 if the following applies:<br>Disorientation (i.e., two or more incorrect answers for questions 1 to 7)<br>1. What is your name?<br>2. What year were you born?<br>3. What city or town do you live in?<br>4. What type of place is this?<br>5. What is the year?<br>6. Who is the current president (or country-specific leader)?<br>7. What is the month?<br>Note: Patients who are in Stage 2 may be sleepy (though easily arousable) but will be responsive and able to engage in conversation with clinical staff, but may be slower to respond. |
| Stage 3 | Patient to be considered Stage 3 if any of the following apply:<br>Gross disorientation/obvious confusion (inappropriate response to questions or commands; bewilderment; inattention to questions)<br>Severe drowsiness (can be aroused by moderate stimuli but then almost immediately drifts back to sleep)<br>Stupor (unresponsiveness from which the patient can be aroused only by vigorous and repeated stimuli; incomprehensible speech)<br>Note: Patients who are in Stage 3 may have severe drowsiness where they can be aroused by moderate stimuli, but then almost immediately drift back to sleep. |
| Stage 4 | Patient to be considered Stage 4 if coma is present.<br>A coma is defined as a state of unarousable unresponsiveness. |

In some embodiments of the methods described herein, the patient being treated for hepatic encephalopathy is suffering from hyperammonemia. In some such embodiments, the patient may have acute liver failure or chronic liver disease, resulting excess ammonia in the bloodstream, and thereof with the manifested symptoms of hepatic encephalopathy. In some further embodiments, the patient has liver cirrhosis (for example, cirrhosis classified as Child Pugh A, B or C), or liver decompensation.

In any embodiments of the methods described herein, the HEST may be used to determine the severity of hepatic encephalopathy (e.g., grade 2, 3, or 4). The HEST may be used by a medical professional (e.g., a doctor, a clinician), or a non-medical professional (e.g., a care giver).

Overt Hepatic Encephalopathy Screening Tool (O-HEST)

Some additional embodiments of the disclosure relate to methods of treating or ameliorating hepatic encephalopathy in a patient in need thereof, comprising: determining the presence of an overt hepatic encephalopathy event by using a hepatic encephalopathy screening tool comprising a first assessment and a second assessment; and administering to said patient an effective amount of a medicament (e.g., one or more ammonia lowering agents) to treat or ameliorate hepatic encephalopathy when the presence of an overt hepatic encephalopathy event is present or has occurred; wherein the first assessment comprises using a set of factual questions to determine whether the patient is disoriented to time or place, and the second assessment comprises determining the level of consciousness of the patient; and wherein the hepatic encephalopathy screening tool does not require observation or determination of asterixis.

Some further embodiments of the disclosure relate to methods of treating or ameliorating hepatic encephalopathy in a patient in need thereof, comprising: receiving information regarding the presence of an overt hepatic encephalopathy event in the patient, wherein the presence of an overt hepatic encephalopathy event is determined by a hepatic encephalopathy screening tool, said screening tool comprising a first assessment and a second assessment; and administering to said patient an effective amount of a medicament (e.g., one or more ammonia lowering agents) to treat or ameliorate hepatic encephalopathy when the presence of an overt hepatic encephalopathy event is present or has occurred; wherein the first assessment comprises using a set of factual questions to determine whether the patient is disoriented to time or place, and the second assessment comprises determining the level of consciousness of the patient; and wherein the hepatic encephalopathy screening tool does not require observation or determination of whether the patient has asterixis.

In some embodiments, the patient is considered disoriented to time if the patient fails to answer two or more questions regarding time correctly, and the patient is considered disoriented to place if the patient fails to answer one or more questions regarding place correctly. In some such embodiments, the set of questions for determining whether a patient is disoriented to time may include questions about year, month, day or the week, and date. In some such embodiments, the set of questions for determining whether a patient is disoriented to place may include questions about the country, the province/state, city/town or the type of place (e.g., hospital or house) that the patient is currently at. In some further embodiments, the factual question does not require determination of whether the patient has been disorientated to person (e.g., no questions related to name of self or family member, etc.).

In one particular embodiment, the factual questions regarding time and place includes the following:

Is the patient disoriented to time?
Documentation:
Knows the year
Knows the month
Knows the day of the week
Knows the date
Is the patient disoriented to place?
Documentation:
Knows the country
Knows the province/state
Knows the city/town
Knows the type of place (e.g., hospital, house)

In some embodiments, the level of consciousness in the second assessment comprises alert and responsive; sleeping but responsive; severe drowsiness, lethargy or somnolence; stuporous; or comatose. For example, when a patient is alert and can engage in conversation, the level of consciousness in the patient may be considered to be alert and responsive. When a patient may be slower to respond when engaged in conversation, the patient may be considered to be sleepy but responsive. In some such embodiments, an overt hepatic encephalopathy event is present if the patient is disoriented to either time or place when the patient's level of consciousness is alert and responsive; or sleeping but responsive. In some other embodiments, an overt hepatic encephalopathy event is present if the patient's level of consciousness is severe drowsiness, lethargy or somnolence; stuporous; or comatose and other causes of altered mental status have been ruled out, such as alcohol intoxication. For example, the level of consciousness of a patient may be considered to be severe drowsiness, lethargy, or somnolence if the patient may need repeated verbal or moderate physical stimuli to initiate a response; drifts back to sleep easily or quickly. The level of consciousness of a patient may be considered to be stuporous if the patient can be aroused only by vigorous and repeated physical stimuli; and the patient likely has incomprehensible speech. The level of consciousness of a patient may be considered to be comatose if the patient is unarousable and unresponsive to any verbal or noxious stimuli.

In some embodiments, the determination of the presence of an overt hepatic encephalopathy event is independent of any determination of classification or grading of hepatic encephalopathy (either using an embodiment of the HEST described herein, or a conventional grading system, such as West Haven (WH) grading system. For example, the caregiver of the medical professional does not have to determine a grade of the hepatic encephalopathy episode(s).

As used herein, the language "the presence of an overt hepatic encephalopathy event in a subject" as used in the methods described herein, includes when the subject is experiencing or has recently experience an overt hepatic encephalopathy episode.

In any embodiments of the methods described herein, the O-HEST may be used by a medical professional (e.g., a doctor, a clinician), or a non-medical professional (e.g., a care giver).

Hepatic Encephalopathy Treatments

A common therapy for patients with hepatic encephalopathy involves strategies to reduce the concentration of ammonia. These include restriction of dietary protein intake; administration of lactulose, neomycin, L-ornithine L-aspartate (LOLA), or sodium benzoate; and cleansing enemas. There are currently marketed products that contain phenylacetic acid (e.g., AMMONUL®) or prodrugs of phenylacetic acid, e.g., phenylbutyrate (BUPHENYL®) or glycerol phenylbutyrate (RAVICTI®) as the ammonia scavenger (binding agent) for the treatment of hyperammonemia due to urea cycle disorder (UCDs). RAVICTI® has also been evaluated in clinical trials and shown preliminary efficacy for the treatment of hepatic encephalopathy. See, for example, Rockey D. et al., "*Randomized, Double-Blind, Controlled Study of Glycerol Phenylbutyrate in Hepatic Encephalopathy*," Hepatology, 2014, 59(3):1073-1083. In addition, L-ornithine phenylacetate has been reported to be an effective treatment of hyperammonemia and hepatic encephalopathy. Jalan et al., reported a clinical study where the data showed that L-ornithine phenylacetate is useful in ammonia lowering. See Jalan et al., "*L-Ornithine phenylacetate (OP): a novel treatment for hyperammonemia and hepatic encephalopathy*," Med Hypotheses 2007; 69(5): 1064-69. See also, U.S. Publication Nos. 2008/0119554, 2010/0280119, and 2013/0211135, each of such is hereby incorporated by reference in its entirety.

Non-limiting examples of the ammonia lowering agent may be used to treat or ameliorate hepatic encephalopathy in any method described herein include a magnesium phosphate product (MGP), a phenylacetic acid prodrug (such as glycerol phenylbutyrate (GPB), sodium phenylacetate, phenylbutyric acid (PBA), or sodium phenylbutyrate (NaPBA)), sodium benzoate, L-arabinose, a laxative (such as a non-absorbable or minimally absorbable disaccharide, e.g., lactulose, lactitol), an antibiotic or antimicrobial agent (e.g., a non-absorbable or minimally absorbable antibiotic, e.g., rifaximin), L-ornithine L-aspartate (LOLA), ornithine in combination with at least one of phenylacetate and phenylbutyrate, or any combination thereof. In some embodiments, the ammonia lowering agent is, or comprises, ornithine in combination with at least one of phenylacetate and phenylbutyrate. In one embodiment, the ammonia lowering agent is L-ornithine phenylacetate.

L-ornithine phenylacetate has been granted orphan drug status by the United States Food and Drug Administration and was granted fast track designation for the treatment of hyperammonemia and resultant hepatic encephalopathy. Currently, L-ornithine phenylacetate is under clinical investigation for the treatment of overt HE in patients with decompensated liver cirrhosis. Patients receive continuous intravenous infusion of L-ornithine phenylacetate at various doses of 5 g, 10 g, 15 g, 20 g or 25 g per day for 1, 2, 3, 4, 5, 6, or 7 days depending on the baseline severity of the liver impairment.

In some embodiments of the methods described herein, the medicament for treating or ameliorating hepatic encephalopathy comprises L-ornithine phenylacetate. In some further embodiments, L-ornithine phenylacetate may be administered in the form of an oral pharmaceutical composition. For example, L-ornithine phenylacetate may be administered in an oral dose of about 2 g, 3 g, 4 g, 5 g, 6 g, 7 g, 8 g, 9 g or 10 g or a range defined by any two of the preceding values. The oral administration of L-ornithine phenylacetate may be at least one time per day (24 hours), two times per day or three times per day. The oral dose of L-ornithine phenylacetate may be in a single unit dosage form or may be in two or more unit dosage forms, such as a tablet, a capsule, a pill, pellets, free-flowing power, or an oral liquid or solution, etc. In some embodiments, the oral administration of L-ornithine phenylacetate is about 2 g twice or three times per day. In some additional embodiments, the oral administration of L-ornithine phenylacetate is about 4 g twice or three times per day.

Alternatively, L-ornithine phenylacetate may be administered intravenously, for example, as intravenous (IV) infusion. The amount of L-ornithine phenylacetate administered via IV infusion may be about 5 g, 6 g, 7 g, 8 g, 9 g, 10 g, 11 g, 12 g, 13 g, 14 g, 15 g, 16 g, 17 g, 18 g, 19 g, 20 g, 21 g, 22 g, 23 g, 24 g, 25 g, 26 g, 27 g, 28 g, 29 g, 30 g, 31 g, 32 g, 33 g, 34 g or 35 g per day, or a range defined by any two of the preceding values. In some such embodiments, the intravenous infusion comprises a loading dose of about 20 g of L-ornithine phenylacetate via 6-hour continuous IV infusion then followed by an intermediate dose of about 15 g L-ornithine phenylacetate via 18-hour continuous IV infusion immediately after the initial loading dose. Then the patient may continue the remainder of the treatment of a maintenance dose for up to 4 days (120 hours) of 15 g L-ornithine phenylacetate/24 hours continuous IV infusion. The treatment may be administered in addition to the standard of care, for example, lactulose with or without rifaximin. In some embodiments, a patient having severe repaired renal or hepatic function may receive reduced dose of L-ornithine phenylacetate described herein, such as about 90%, 80%, 70%, 60%, or 50% by weight of the standard dose of L-ornithine phenylacetate.

EXAMPLES

The following examples, including experiments and results achieved, are provided for illustrative purposes only and are not to be construed as limiting the present application.

Example 1

In this example, the evaluation of the validity and responsiveness of the hepatic encephalopathy staging tool (HEST) in a Phase 2B safety, efficacy, and tolerability study of L-ornithine phenylacetate in hospitalized patients with cirrhosis and associated hyperammonemia with an episode of hepatic encephalopathy. As summarized below, the HEST was shown to be valid and responsive to change using a variety of statistical tests.

Materials and Methods

The data for this study came from the Phase 2B, multi-center, randomized, double-blind, placebo-controlled study evaluating L-ornithine phenylacetate administered via continuous 24-hour intravenous (IV) infusion to hospitalized subjects with cirrhosis and associated hyperammonemia with an acute episode of hepatic encephalopathy Stage 2-4.

All subjects were stratified at time of randomization by 1) model for end-stage liver disease (MELD) score (less than or equal to 30 versus greater than 30), and 2) Hepatic Encephalopathy Staging Tool (Stage 2 versus Stage 3/4) using an interactive voice/web-response randomization system. A third stratification grouped North American investigational centers according to liver transplantation frequency (≥70 transplants per year versus <70 transplants per year). Outside of North America, stratification was employed with the same MELD and Hepatic Encephalopathy Staging Tool thresholds delineated above.

The primary endpoint was time to confirmed clinical response defined for subjects with Baseline Stage 3 (stupor) or 4 (coma) hepatic encephalopathy as a reduction to Stage 2, and for subjects with Baseline Stage 2 hepatic encephalopathy as improvement to Stage 0/1 using the HE Staging Tool.

Assessments of HE, specifically the HE Staging Tool, Glasgow Coma Scale (GCS), modified orientation log (MO-Log) were conducted by trained investigators, sub-investigators, nurse practitioners, or physician's assistants. The Physician Overall Treatment Evaluation (OTE) of Hepatic Encephalopathy and Physician Ranked Assessments (specific items) performed in the time interval between end-of-final infusion and three hours post end-of-final-infusion were performed by a physician, which was the same assessor as the Screening or Baseline evaluator to ensure accuracy of the ranking relative to pretreatment status (same, better, worse).

Table 1 below describes the hepatic encephalopathy staging tool:

TABLE 1

| | |
|---|---|
| Stage 0/1 | No asterixis* and no disorientation based on the following 5 questions (i.e., patient provides correct response to Questions 1, 2, 3, 4, and 5):<br>1. What is your name?<br>2. What city are we in?<br>3. What type of place is this? (correct answer hospital)<br>4. What is the year?<br>5. What is the month? |
| Stage 2 | Asterixis* and disorientation based on the following 5 questions, i.e., any single incorrect response qualifies the patient as Stage 2 for the following questions 1, 2, 3, 4, or 5:<br>1. What is your name?<br>2. What city are we in?<br>3. What type of place is this? (correct answer hospital)<br>4. What is the year?<br>5. What is the month? |
| Stage 3 | Stupor, arousable but falls asleep, responsive to verbal stimuli<br>Obvious confusion<br>Gross disorientation |
| Stage 4 | Coma |

*Observe patient for 30 seconds; 3 or more flaps in that timeframe is considered positive for asterixis For a patient to qualify for study entry as Stage 2 HE, both asterixis and at least one error in the 5 sentinel questions must be present. Either alone is not sufficient to allow enrollment. For recording HE response during (or after) study treatment: For all time points after start of study drug infusion no patient can be classified as improved to Stage 0/1 unless both asterixis is resolved and all 5 questions are answered correctly.

The GCS scale is standardized scoring system quantifying the degree of consciousness in the critically ill and for predicting the duration and ultimate outcome of coma, primarily in patients with head injuries. The system involves eye opening, verbal response, and motor response, all of which are evaluated independently according to a rank order that indicates the level of consciousness and degree of dysfunction. Scoring is determined by three factors: amount of eye opening, verbal responsiveness, and motor responsiveness. Scores for the three factors are summed to produce an overall score that ranges from 3 (worst) to 15 (best). The Glasgow Coma scale is displayed in Table 2. The classification of head injuries using the GCS is generally as follows:

Severe: GCS score≤8
Moderate: 9≤GCS score≤12
Mild: 13≤GCS score≤15

TABLE 2

| Characteristic | Score |
|---|---|
| Eyes Open | |
| Spontaneous (eyes open does not imply awareness) | 4 |
| To speech (any speech, not necessarily a command) | 3 |
| To pain (should not use supraorbital pressure for pain stimulus) | 2 |
| Never | 1 |

TABLE 2-continued

| Characteristic | Score |
| --- | --- |
| Best Verbal Response | |
| Oriented (to time, person, place) | 5 |
| Confused speech (disoriented) | 4 |
| Inappropriate (swearing, yelling) | 3 |
| Incomprehensible sounds (moaning, groaning) | 2 |
| None | 1 |
| Best Motor Response | |
| Obeys commands | 6 |
| Localizes pain (deliberate or purposeful movement) | 5 |
| Withdrawal (moves away from stimulus) | 4 |
| Abnormal flexion (decortication) | 3 |
| Extension (decerebration) | 2 |
| None (flaccidity) | 1 |

Modified Orientation Log (MO-Log) was developed to measure orientation to time, place, and circumstance in a rehabilitation population. It tests for orientation using a systematic approach that starts with free recall, if that is incorrect, it then goes to a logical cue, failing which a multiple-choice option is provided (which gives each question a maximum of three and a minimum of zero points). The MO-Log has eight simple questions and a score ranging from 0 through 24 (24 being normal). Five questions are based on time (including ability to read clock time), and three are based on place. Each question is scored on a 0 to 3 scale based on the type of response provided by the patient, as follows:

Scoring: (see standardized questions) The Modified Orientation Log (MO-Log)

3 points=correct spontaneously or upon first free recall attempt
2 points=correct upon logical cueing
1 point=correct upon multiple choice cueing
0 point=unable, incorrect, inappropriate response Total score in the above tabular grid is the sum of all points obtained for individual items (minimum 0, maximum 24)

The Physician Overall Treatment Evaluation (OTE) is a ranking of better, about the same, or worse, relative to pre-treatment hepatic encephalopathy status.† If the ranking is better or worse, it is then followed by a global assessment of the degree of change in the patient's hepatic encephalopathy by selecting among seven options:

1. Almost the same, hardly any better (worse) at all
2. A little better (worse)
3. Somewhat better (worse)
4. Moderately better (worse)
5. A good deal better (worse)
6. A great deal better (worse)
7. A very great deal better (worse)

This two-stage rating process produces a score that ranges from −7 (worse gradations) to +7 (better gradations) on a 15-point scale, where zero (0) indicates no change.

The Physician Ranked Assessment is a ranking of better, about the same, or worse, relative to pretreatment status in three domains: level of consciousness, orientation, and asterixis. Ranking of level of consciousness is performed first. However, orientation and asterixis are rated only if level of consciousness is improved. For each component, if the global ranking is better or worse, it is followed by an assessment of degree of change using a Likert scale with the following five choices:

1. Almost the same, hardly any better (worse) at all
2. Somewhat better (worse)
3. Moderately better (worse)
4. A good deal better (worse)
5. A very great deal better (worse)

This two-stage rating process produces a score for each domain that ranges from −5 (worse gradations) to +5 (better gradations) on an 11-point scale, where zero (0) indicates no change.

Statistical Analysis

The methods used to demonstrate the validity of the HEST are convergent validity, discriminant validity, and predictive validity. Each of these methods involves the use of conceptually related criterion variables. Convergent validity is the degree of agreement between measurements of the same trait obtained by different approaches supposed to measure the same trait and is normally assessed as the correlation between the scale and the criterion variables. Discriminant validity means that the scale can discriminate between different levels of the trait being measured according to a priori hypotheses. Predictive validity is similar to convergent validity except that the criterion variable is measured at a later time, not concurrently.

Several criterion measures collected as part of the Phase 2B study were used to evaluate the validity of the HE Staging Tool: the MO-Log, the GCS, the Physician OTE, and Physician Ranked Assessments.

Responsiveness refers to the ability of a scale to detect clinically meaningful changes in the trait being measured. To evaluate the responsiveness of the HEST, the Physician OTE and the Physician Ranked Assessments (level of consciousness, orientation, and asterixis) were used as indicators of clinically meaningful changes. Two approaches were used to evaluate responsiveness—correlation analysis and analysis of variance.

Change in HE stage was calculated by subtracting HE stage at baseline from the HE stage at the corresponding time point where the OTE and ranked assessments were completed (three hours post-treatment). For this purpose, HE Stage 0/1 used the value of 1. For example, if a patient was determined to be at Stage 3 at baseline and at Stage 0/1 post-treatment, change in HE stage=1−3=−2.

The correlation analysis was conducted in two ways, taking advantage of the fact that both the OTE and ranked assessment scores are determined using two steps. In the first step, the patient is rated as better, about the same, or worse relative to pre-treatment hepatic encephalopathy. Spearman rank correlation was used to measure the strength of the relationship between change in HE stage and global assessment of better, about the same, or worse in the following physicians' assessments:

1. OTE
2. Ranked assessment of level of consciousness
3. Ranked assessment of orientation
4. Ranked assessment of asterixis Results In conclusion, convergent validity was excellent with the correlation between the HEST and all three types of criterion measures being well above 0.3 (in absolute value), with (absolute) correlation coefficients ranging between 0.62 and 0.76. Further, the level of agreement across the four common items of the HE Staging Tool and the MO-Log was very good, with Kappa indicating substantial (0.73) to nearly perfect (0.84-0.88) agreement across these four questions.

The HEST also showed excellent discriminant validity with mean scores for both the Glasgow Coma Scale and the MO-Log decreasing significantly as HE stage increased from 0/1 to 4.

Responsiveness analyses indicated significant association between physician Overall Treatment Evaluation (OTE), ranked assessments of consciousness and orientation, and HE Stage change scores. Correlations ranged from −0.69 to −0.40. For ranked assessment of asterixis the strength of the association was lower at approximately 0.22. ANOVA analyses mirrored these results indicating that there were significant differences that varied in the expected direction in mean scores of all four types of physician assessments, across HE stage change category.

Example 2

In this example, a web-based survey was developed to collect data from clinicians in order to assess the inter- and intra-rater reliability of the HEST described in Table 1. The survey was administered twice to participants, with about one week between administrations (Round 1 and Round 2). Five video vignettes depicting patients (actors) in various stages of HE were developed and presented in random order for each survey administration. Clinicians rated the vignettes using the HEST grading system in each survey round. The Round 1 survey also solicited participants' feedback on the utility and clarity of the HEST, their interpretation of asterixis, and their feedback on the HEST instructions. The Round 2 survey mirrored the Round 1 survey, however no open-ended feedback questions were included. Thus, Round 2 survey participants were asked only to view and then rate the same five patient vignettes (again, presented in random order). This report describes the methods and results of this reliability survey study.

Ninety-eight clinician participants were invited to participate in the study. A total of 50 (38 US-based and 12 ex-US) completed the Round 1 survey and were invited to complete the Round 2 survey. Forty-two clinicians (31 US-based and 11 ex-US) completed the Round 2 survey.

Nearly all participants correctly rated four out of the five patient vignettes in the Round 1 survey; 49 participants (98.0%) rated Vignettes A, C and E correctly while all 50 participants (100%) correctly rated Vignette D (Stage 4; coma). Thirty-three participants (66.0%) correctly rated a vignette (Vignette B) that was designed to be a Stage 2 HE episode. This particular scenario involved a patient asleep in the waiting room and who was slow to wake as the nurse gently tapped him and called his name. One third of participants (n=16, 32.0%) rated this vignette as Stage 3 due to the patient's somnolence and one participant rated it as Stage 0/1. Qualitative comments from the clinician participants noted ambiguity with the HEST Stage 3 definition which led to modifications for clarity in the Stage 3 definition.

Overall, the HEST demonstrated excellent inter-rater and intra-rater (test-retest) reliability. Qualitatively, clinician participants generally had positive views of the HEST and widely agreed with its operational definition of asterixis (i.e., 3 or more flaps in 30 seconds) as well as its definitions for Stages 2, 3, and 4.

In conclusion, the HEST demonstrated excellent inter-rater and intra-rater reliability and was viewed positively by a large group of seasoned hepatologists. Modifications to the Stage 3 definition of the HEST (as shown in the table below) were made based upon clinician ratings and qualitative responses to Vignette B, and additional feedback from three clinicians following the survey. These modifications should enhance HE rating accuracy for future clinical trial use.

| Stage | Description |
|---|---|
| Stage 0/1 | Patient to be considered Stage 0/1 if any of the following apply:<br>No asterixis*/No disorientation (i.e., correct answers to all 5 questions below)<br>No asterixis*/Yes disorientation (i.e., 1 or more incorrect answers to 5 questions below)<br>Yes asterixis*/No disorientation (i.e., correct answers to all 5 questions below)<br>1. What is your name?<br>2. What city are we in?<br>3. What type of place is this? (correct answer hospital)<br>4. What is the year?<br>5. What is the month? |
| Stage 2 | Patient to be considered Stage 2 if the following applies:<br>Yes asterixis*/Yes disorientation (i.e., 1 or more incorrect answers to 5 questions below)<br>1. What is your name?<br>2. What city are we in?<br>3. What type of place is this? (correct answer hospital)<br>4. What is the year?<br>5. What is the month?<br>Note: patients who are sleepy, but easily arousable and responsive to questions, can qualify as HEST Stage 2 if appropriate |
| Stage 3 | Patient to be considered Stage 3 if any of the following apply:<br>Severe drowsiness (can be aroused by moderate stimuli but then almost immediately drifts back to sleep)<br>Stupor (unresponsiveness from which the patient can be aroused only by vigorous and repeated stimuli; incomprehensible speech)<br>Obvious confusion/gross disorientation (inattention to questions; inappropriate response to commands or questions; bewilderment) |
| Stage 4 | Patient to be considered Stage 4 if coma is present.<br>A coma is defined as a state of unarousable unresponsiveness. |

*Observe patient for 30 seconds; 3 or more flaps in that timeframe is considered positive for asterixis.

Example 3

In this example, an overt hepatic encephalopathy screening tool (OHEST) was developed to document the presence or absence of an overt hepatic encephalopathy (OHE) event (see Table 3). The patient is considered to be having (or have had) an OHE event if the patient is disoriented to time or place, or if the patient is unable to be assessed due to altered level of consciousness. Other potential causes of altered mental status (e.g., alcohol intoxication) must be reasonably ruled out before confirming an OHE event.

When using the OHEST, it is required that source of information for OHEST documentation be identified (e.g., clinician-observed, caregiver input, observed by outside medical professional, review of medical records, or virtual visit, etc.). Other potential causes of altered mental status (e.g., alcohol intoxication, sleep deprivation) must be reasonably ruled out before confirming an OHE event. In some instances, clinical findings should be present for at least 1 hour to be considered an OHE event.

TABLE 3

Is the patient disoriented to time?
Documentation:
Knows the year
Knows the month
Knows the day of the week
Knows the date
Is the patient disoriented to place?
Documentation:
Knows the country
Knows the province/state
Knows the city/town
Knows the type of place (e.g., hospital, house)

Please select one response below that best describes the patient's level of consciousness.

| Alert and responsive (Patient is alert and can engage in conversation) | Sleepy but responsive (Patient may be slower to respond when engaged in conversation) | Severe drowsiness, lethargy, or somnolence (Patient may need repeated verbal or moderate physical stimuli to initiate a response; drifts back to sleep easily or quickly) | Stuporous (Patient can be aroused only by vigorous and repeated physical stimuli; patient likely has incomprehensible speech) | Comatose (Patient is unarousable and unresponsive to any verbal or noxious stimuli) |
|---|---|---|---|---|

If a patient answers two or more of the four "time" questions incorrectly, the patient is considered to be disoriented to time and will be documented as having an OHE event. If a patient answers one or more of the four "place" questions incorrectly, the patient is considered to be disoriented to place and will be documented as having an OHE event. People who are disoriented to place (typically viewed as more serious than disorientation to time) are generally already disoriented to time. If a patient is identified to be either "alert and responsive" or "sleepy but responsive", an OHE event has occurred ONLY if patient is disoriented to either time or place. Patients who are experiencing more severe stages of hepatic encephalopathy (i.e., Stages 3 or 4) are unlikely to engage in any meaningful conversation or be able to respond to the orientation questions. Therefore, these patients will be documented as having an OHE event based primarily on their level of consciousness ("severe drowsiness, lethargy, or somnolence", "stuporous", or "comatose"). The OHEST does not rely on the presence or absence of asterixis in the determination of HE severity.

What is claimed is:

1. A method of treating or ameliorating hepatic encephalopathy in a patient in need thereof, comprising:
    assessing or receiving information regarding the severity of hepatic encephalopathy in the patient, wherein the severity of hepatic encephalopathy is assessed by a hepatic encephalopathy staging tool, said staging tool comprising a first criterion, a second criterion, a third criterion and a fourth criterion;
    administering to the patient an effective amount of an ammonia lowering agent, wherein the ammonia lowering agent is L-ornithine phenylacetate, to treat or ameliorate hepatic encephalopathy;
    wherein the first criterion comprises a first set of 4-8 factual questions designed to assess whether the patient has any disorientation, and wherein the first criterion is met when the patient verbally answers all the factual questions correctly, or when the patient verbally answers only one factual question incorrectly,
    wherein the second criterion comprises a second set of 4-8 factual questions designed to assess whether the patient has any disorientation, and wherein the second criterion is met when the patient answers two or more factual questions incorrectly,
    wherein the third criterion is met when at least one symptom is observed or has been observed in the patient, the symptom is selected from the group consisting of stupor, severe drowsiness, obvious confusion, and gross disorientation, wherein the fourth criterion is met when the patient is in a coma,
    wherein the severity of hepatic encephalopathy in the patient is categorized into stages, wherein the first stage is defined by meeting the first criterion, the second stage is defined by meeting the second criterion, the third stage is defined by meeting the third criterion and the fourth stage is defined by meeting the fourth criterion, and
    wherein the administration of the L-ornithine phenylacetate is based on the assessed severity of hepatic encephalopathy, and
    assessing or receiving information regarding the severity of hepatic encephalopathy in the patient by the hepatic encephalopathy staging tool after the administration of the L-ornithine phenylacetate to determine the effectiveness of the hepatic encephalopathy treatment; and
    adjusting the amount of the L-ornithine phenylacetate based on the effectiveness of the hepatic encephalopathy treatment.

2. The method of claim 1, wherein the hepatic encephalopathy staging tool does not require observation or determination of asterixis.

3. The method of claim 1, wherein the first set factual questions and the second set of factual questions each comprises inquiry to the patient's name, residence, birthday, time, present location, or other facts that are widely or commonly known, or combinations thereof.

4. The method of claim 3, wherein the first set of factual questions and the second set of factual questions each comprises five to seven questions.

5. The method of claim 3, wherein the first set of factual questions are the same as the second set of factual questions.

6. The method of claim 1, wherein the patient is suffering from hyperammonemia, or the patient has acute liver failure, chronic liver disease, liver cirrhosis, or liver decompensation.

7. The method of claim 1, wherein L-ornithine phenylacetate is administered orally or by intravenous infusion.

8. The method of claim 1, wherein the first stage of hepatic encephalopathy has two sub-stages.

9. A method of treating or ameliorating hepatic encephalopathy in a patient in need thereof, comprising:
assessing or receiving information regarding the severity of hepatic encephalopathy in the patient, wherein the severity of hepatic encephalopathy is assessed by a hepatic encephalopathy staging tool, said staging tool comprising a first criterion, a second criterion, a third criterion and a fourth criterion;
administering to the patient an effective amount of an ammonia lowering agent, wherein the ammonia lowering agent is L-ornithine phenylacetate, to treat or ameliorate hepatic encephalopathy;
wherein the first criterion comprises a first set of 4-8 factual questions designed to assess whether the patient has any disorientation, and wherein the first criterion is met when the patient verbally answers all the factual questions correctly and the patient does not have asterixis,
wherein the second criterion comprises a second set of 4-8 factual questions designed to assess whether the patient has any disorientation, and wherein the second criterion is met when the patient fails to verbally answer all the factual questions correctly and the patient has asterixis,
wherein the third criterion is met when at least one symptom is observed or has been observed in the patient, the symptom is selected from the group consisting of stupor, severe drowsiness, obvious confusion, and gross disorientation,
wherein the fourth criterion is met when the patient is in a coma,
wherein the severity of hepatic encephalopathy in the patient is categorized into stages, wherein the first stage is defined by meeting the first criterion, the second stage is defined by meeting the second criterion, the third stage is defined by meeting the third criterion and the fourth stage is defined by meeting the fourth criterion,
wherein the administration of the L-ornithine phenylacetate is based on the assessed severity of hepatic encephalopathy, and
assessing or receiving information regarding the severity of hepatic encephalopathy in the patient by the hepatic encephalopathy staging tool after the administration of the L-ornithine phenylacetate to determine the effectiveness of the hepatic encephalopathy treatment; and
adjusting the amount of the L-ornithine phenylacetate based on the effectiveness of the hepatic encephalopathy treatment.

10. The method of claim 9, wherein the first stage of hepatic encephalopathy has two sub-stages.

11. The method of claim 9, wherein the first set factual questions and the second set of factual questions each comprises inquiry to the patient's name, residence, birthday, time, present location, or other facts that are widely or commonly known, or combinations thereof.

12. The method of claim 11, wherein the first set of factual questions and the second set of factual questions each comprises five to seven questions.

13. The method of claim 11, wherein the first set of factual questions are the same as the second set of factual questions.

14. The method of claim 9, wherein the patient is suffering from hyperammonemia, or the patient has acute liver failure, chronic liver disease, liver cirrhosis, or liver decompensation.

15. The method of claim 9, wherein L-ornithine phenylacetate is administered orally or by intravenous infusion.

* * * * *